United States Patent
Santus (10) Patent No.: US 6,280,761 B1
(45) Date of Patent: Aug. 28, 2001

(54) NICOTINE LOZENGE

(75) Inventor: Gian Carlo Santus, Milan (IT)

(73) Assignee: Pharmacia AB, Helsingborg (SE)

( * ) Notice: Subject to any disclaimer, the term of this patent is extended or adjusted under 35 U.S.C. 154(b) by 0 days.

(21) Appl. No.: 08/644,971

(22) Filed: May 15, 1996

Related U.S. Application Data (62) Division of application No. 08/097,962, filed on Jul. 26, 1993, now Pat. No. 5,549,906.

(51) Int. Cl.[7] ............................................. A61K 9/20
(52) U.S. Cl. ................................... 424/435; 424/440
(58) Field of Search ................................... 424/440, 435

(56) References Cited

U.S. PATENT DOCUMENTS

| | | | |
|---|---|---|---|
| Re. 34,089 | 10/1992 | Kydonieus et al. | 424/449 |
| 4,753,800 | 6/1988 | Mozda et al. | 424/440 |
| 4,806,356 | 2/1989 | Shaw | 424/440 |
| 4,837,027 | 6/1989 | Lee et al. | 424/449 |
| 4,907,605 | 3/1990 | Ray et al. | 131/270 |
| 4,908,213 | 3/1990 | Govil et al. | 424/447 |
| 4,946,853 | 8/1990 | Bannon et al. | 415/343 |
| 4,953,572 | 9/1990 | Rose et al. | 131/270 |
| 5,004,601 | 4/1991 | Snipes | 424/78 |
| 5,016,652 | 5/1991 | Rose et al. | 131/270 |
| 5,055,478 | 10/1991 | Cooper et al. | 514/343 |
| 5,069,904 | 12/1991 | Masterson | 424/401 |
| 5,135,752 | 8/1992 | Snipes | 424/435 |
| 5,135,753 * | 8/1992 | Baker et al. | 424/435 |
| 5,139,790 | 8/1992 | Snipes | 424/435 |
| 5,156,845 | 10/1992 | Grodberg | 424/440 |
| 5,174,989 | 12/1992 | Tanaka et al. | 424/52 |
| 5,362,496 * | 11/1994 | Baker et al. | 424/435 |

FOREIGN PATENT DOCUMENTS

| | | |
|---|---|---|
| 0899037 | 6/1964 | (BE) . |
| 1273878 | 1/1988 | (CA) . |
| 0192950 | 1/1986 | (EP) . |
| 2142822 | 1/1985 | (GB) . |
| 2227659 | 8/1990 | (GB) . |
| 2230439 | 10/1990 | (GB) . |
| 2255892 | 11/1992 | (GB) . |
| 8803803 | 6/1988 | (WO) . |
| 9101132 | 2/1991 | (WO) . |
| 9102518 | 3/1991 | (WO) . |
| 9109599 | 7/1991 | (WO) . |

OTHER PUBLICATIONS

Pharmetrix—"Nicotine Smoking Cessation Therapeutic Systems," Technology Overview, May 12, 1993, Copy No. 32, Pharmetrix Corp.

Lee, Emmet W. et al. "Cigarette Smoking, Nicotine Addiction, & Its Pharmacologic Treatment," *Arch Intern Med*/vol. 153, Jan. 11, 1993.

Sachs, David P.L. et al. "Effectiveness of a 16–Hour Transdermal Nicotine Patch in a Medical Practice Setting, Without Intensive Group Counseling," In Press: *Arch Int Med*.

Smith, Eric W. et al. "The Local Side Effects of Transdermally Absorbed Nicotine," *Skin Pharmacol* 1992:5:69–76.

McKenna, James P. et al. "Transdermal Nicotine Replacement and Smoking Cessation," *American Family Physician* Jun. 1992 p. 2595–2601.

Fiore, Michael C. et al. "Tobacco Dependence and the Nicotine Patch," *JAMA*, Nov. 18, 1992 vol. 268, No. 19 p. 2687–2694.

"Correspondence," *The New England Journal of Medicine*, Jan. 30, 1992, vol. 326 No. 5, p. 344–345.

(List continued on next page.)

Primary Examiner—Jyothsan Venkat
(74) Attorney, Agent, or Firm—Pravel, Hewitt, Kimball & Krieger (57) ABSTRACT

A method for smoking cessation therapy is described that utilizing an improved nicotine lozenge to satisfy transient craving. The lozenge contains nicotine, a nonnutritive sweetener and an absorbent excipient.

3 Claims, 2 Drawing Sheets

OTHER PUBLICATIONS

Product Insert for Prostep™ (nicotine transdermal system), Lederle Laboratories, 1992.

Soderling, Eva, et al. "Perspectives on xylitol–induced oral effects," Proc Finn Dent Soc 1991 87 No. 2.

Product Insert for Habitrol™ nicotine, Transdermal Therapeutic System, Basel Pharmaceuticals, 1991.

Sachs, David P.L. "Advances in Smoking Cessation Treatment*," Reprinted from Current Pulmonology, Chap. 6, vol. 12, 1991, p. 140–197.

Tonneson, Philip et al. "A Double–Blind Trial of a 16–Hour Transdermal Nicotine Patch in Smoking Cessation," *The New England Journal of Medicine* vol. 325, No. 5, 1991, p. 311–315.

Sachs, David P.L. et al. "Pharmacologic Approaches to Smoking Cessation,"*Clinics in Chest Medicine*—vol. 12, No. 4, Dec. 1991 p. 769–791.

Bradlet, J. R. et al. "Buccal Absorption of Nicotine from Smokeless Tobacco Sachets," *The Lancet,* Dec. 14, 1985 p. 1370.

Gourlay, Steven G. et al. "Antismoking products," *The Medical Journal of Australia* vol. 153 Dec. 3/17, 1990 p. 699–707.

U.S. Department of Health and Human Services. "The Health Benefits of Smoking Cessation," U.S. Dept.of Health & Human Services Public Health Service, Centers for disease Control, Center for Chronic Disease Prevention & Health Promotion, Office on Smolind & Health. DHHS Publication No. (DCD) 90–8416, 1990.

Muller, Ph. et al. "The Use of Transdermal Nicotine in Smoking Cessation," *Lung* Springer–Verlag, New York Inc. 1990, p. 445–453.

Olinger, Philip M. "Sweetening Sugar–Free Medications: Xylitol," Presented at Interphex•USA Conference/Exhibition, May 8–11, 1990, New York.

Steuer, Jill D. et al. "Cigarette Craving and Subsequent Coping Responses Among Smoking Cessation Clinic Participants," *Steuer*—vol. 16, No. 2, 1989, p. 193–198.

Sachs, David P.L. "Nicotine Polacrilex: Practical Use Requirements*," *Curr Pulmonol,* Chapter 7, 10:141–158, 1989.

Excerpt from *Oral Drug Delivery* "Oral Mucosal Drug Delivery," 1989, Chapter 3, p. 183–190.

Graffner, Christina "Clinical experience with novel buccal and sublingual administration," *Novel Drug Delivery and Its Therapeutic Application,* Chapter 16, 1989, p. 159–165.

Sachs, David P.L. "Transdermal Nicotine for Smoking Cessation—Six–Month Results From Two Multicenter Controlled Clinical Trials,"*JAMA,* Dec. 11, 1991—vol. 266, No. 22, p. 3133–3138.

Sachs, David P.L.et al. "Are Smokers Trying to Stop and Smokers Not Trying to Stop the Same Experimental Model?," *Research* Monograph Series, Problems of Drug Dependence 1989, Proceedings of the 51st Annual Scientific Meeting, The Committee on Problems of Drug Dependence, Inc., U.S. Dept. of Health and Human Servies, p. 366–367 & Slide Sheets p. 1–7.

Pilot Study for "The Optimum Dose and Schedule for Nicotine Polacrilex Use," National Institute on Drug Abuse U.S. Public Health Service, 1988–1993, p. 775.1–775.9.

Russell, Michael A.H. "Nicotine Replacement: The Role of Blood Nicotine Levels, Their Rate of Change, and Nicotine Tolerance," Nicotine Replacement: A Critical Evaluation, 1988, p. 63–94.

Makinen, Kauko K. "Sweeteners and prevention of dental caries," Preventative, Sep. 1988, vol. 78/No. 9, p. 57–66.

Sachs, David P.L. "Pharmocologic, Neuroendocrine, and Bio–behaviorial Basis for Tobacco Dependence*," *Curr Pulmonol* 8:371–406, 1987.

Warburton, David M. et al. "Facilitation of learning and state dependency with nicotine," *Psychopharmacology* (1986) 89:55–59.

Machacek, Dwaine A. et al. "Quantification of Cotinine in Plasma and Saliva by Liquid Chromatography," *Clinical Chemistry* vol. 32, No. 6, 1986 p. 979–982.

Sachs, David P.L."Cigarette Smoking—Health Effects & Cessation Strategies," Clinics in Geriatric Med.vol. 2, No. 2, May 1986 p. 337–362.

Sachs, David P.L. "Nicotine Polacrilex: Clinical Promises Delivered & Yet to Come," The Pharmacologic Treatment of Tobacco Dependence: Proceedings of the World Congress, Nov. 4–5 1985, p. 120–140.

Russell M.A.H. et al. & Bradley, J. R. et al. "Buccal Absorption of Nicotine From Smokeless to Tobacco Sachets," & "Aortic Valve Replacement in Chronic Renal Failure," *The Lancet* Dec. 14, 1985, p. 1370.

West, R. J. et al. "Effect of Nicotine Replacement on the Cigarette Withdrawal Syndrome," *British Journal of Addiction* 79 (1984) p. 215–219.

Hughes, John R. et al. "Effect of nicotine on the tobacco withdrawal syndrome*," *Psychopharmacology* (1984) 83:82–87.

Wesnes, Keith et al. "Effects of scopolamine and nicotine on human rapid information processing performance," *Psychopharmacology* (1984) 82:147–150.

Benowitz, Neal L. et al. "Smokers of Low–Yield Cigarettes Do Not Consume Less Nicotine," Reprinted from *The New England Journal of Medicine* 309:139–142 (Jul. 21), 1983.

Szeztli, I. "Cyclodextrins and their inclusion complexes," Akademiai Kiado: Budapest, 1992, p. 109.

Harrington, Neil "The craving factor in the treatment of smoking," Br. J. Soc. Clin. Psychol. (1978), 17, p. 363–371.

Jarvik, M.E. et al. "Inhibition of cigarette smoking by orally administered nicotine," *Clinical Pharmacology & Therapeutics* vol. 11, No. 4, 1970, p. 574–576.

Encyclopedia of Chemical Technology, Third Edition, vol. 9, p. 198 (1980).

Encyclopedia of Chemical Technology, Third Edition, vol. 15, p. 568 (1981).

The Merck Index, An Encyclopedia of Chemicals, Drugs, and Biologicals, Tenth Edition, p. 5183 (1983).

EMDEX®(Dextrates, NF Hydrated), Revised Nov., 1995, pp. 1–4.

* cited by examiner

NICOTINE LOZENGE

This is a division of application Ser. No. 08/097,962, filed Jul. 26, 1993 now U.S. Pat. No. 5,549,906.

BACKGROUND OF THE INVENTION

This invention pertains to compositions and therapeutic methods for reducing the craving for nicotine and for smoking cessation. More particularly, this invention is directed to improved compositions of nicotine lozenges and therapeutic methods to provide periodic doses of nicotine to persons who are attempting to quit smoking.

Nicotine replacement therapy as an aid to quitting smoking has been become increasingly popular. Nicotine chewing gum (nicotine polacrilex) and transdermal nicotine are two of the more popular forms of nicotine replacement available commercially. It has become clear, however, that the mere replacement of cigarettes with another nicotine source may not be sufficient to insure success in smoking cessation therapy. Specifically, conventional nicotine replacement therapy does not adequately address the symptoms associated with the cessation of smoking.

Of the many smoking withdrawal symptoms, craving for cigarettes is one of the most difficult to alleviate. As described in Steuer, J. D. and Wewers, M. E. in *Oncology Nursing Forum* 1989, 16, 193–198, cigarette craving is one of the most consistent, most severe, and earliest withdrawal symptoms experienced by those attempting to quit smoking. Some reports suggest that craving peaks over the first 24 to 72 hours of abstinence and then declines, although craving has been reported after five years of abstinence.

Research is focusing on the factors that precipitate craving in an attempt to better understand and deal with the problem of relapse. Some investigators believe that certain smokers are much more likely than others to experience craving symptoms, especially when trying to quit smoking. Based on literature reports and his own investigations, Harrington (in *Br. J. Soc. Clin. Psychol.* 1978, 17, 363–371) reported that smokers can be separated by craving versus noncraving status, and that these separate populations have different responses to smoking cessation therapy. (In his study, treatment consisted of various behavioral strategies, and nicotine replacement was not used.) In particular, abstinence during treatment and success at the end of treatment were significantly related to being a noncraver.

Most commercially available products for nicotine replacement in smoking cessation therapy have not specifically addressed the issue of satisfying craving for nicotine. Instead, as mentioned above, they have generally been targeted towards providing a stable baseline level of nicotine in the blood. Some evidence indicates that low consistent blood levels of nicotine (as provided by transdermal nicotine, and to a lesser extent by nicotine gum) relieve some of the symptoms of nicotine withdrawal, but craving symptoms may not be among these (see Russell, M. A. H. in *Nicotine Replacement: a Critical Evaluation;* Pomerleau, O. F. and Pomerleau, C. S., Eds.; Alan R. Liss, Inc.: New York, 1988; pp 63–94). This may be because cigarette smoking provides an initial sharp rise in blood level, which is missing in these nicotine replacement therapies. The blood level peak produced by cigarettes is both higher (between 30–40 ng/mL) and sharper (this peak is attained within 10 minutes) than the steadier levels obtained from gum or a transdermal system. Russell states that the optimal steady-state blood level for nicotine replacement is between 10–15 ng/mL, but that quick-rise effects are probably necessary for more complete relief from craving in the early stages of cigarette withdrawal. His investigations have indicated that a rise in nicotine blood level of at least 10 ng/mL in 10 minutes is required to obtain postsynaptic effects at nicotinic cholinergic receptors in the central nervous system and at autonomic ganglia. These postsynaptic effects may be responsible for drug-like "high" feelings such as lightheadedness or dizziness experienced by cigarette smokers.

As mentioned above, nicotine gum (nicotine polacrilex) is one of the commercially available sources of nicotine for replacement therapy. Nicotine gum is actually an ion-exchange resin that releases nicotine slowly when the patient chews, and the nicotine present in the mouth is delivered directly to the systemic circulation by buccal absorption. However, much of the nicotine is retained in the gum through incomplete chewing or is largely wasted through swallowing, so that the systemic bioavailability of nicotine from gum is low and averages only 30–40%. Moreover, compared with cigarette smoking, nicotine gum is a slow and inefficient source of nicotine.

Nicotine replacement through transdermal nicotine systems is another therapy that has become commercially available. These nicotine patches provide a low, consistent blood level of nicotine to the user, and bypass the first pass effects of the gut and liver. Transdermal nicotine systems can be designed to provide higher steady-state blood levels of nicotine, but are unable to provide blood level peaks or to provide a rapid increase in blood level. Thus both nicotine gum and transdermal nicotine compete with each other as products providing steady-state nicotine blood levels, but do not satisfy craving symptoms for cigarettes in some smokers.

Other nicotine replacement products that are on the market or have been proposed in the literature have not been of serious interest in smoking cessation therapy, because of problems related to their use, and also because of limited ability to satisfy craving for cigarettes. Nicotine vapor has been delivered to patients in aerosol form, similar to the inhaler technology used to supply bronchial asthma medications, and in a "smokeless cigarette" such as that marketed by Advanced Tobacco Products under the trade name Favor®. Some data indicate, however, that these modes of nicotine delivery do not result in significant nicotine blood levels in patients after use. In addition, inhalation of these nicotine vapor products may be too irritating to the mucosa to be tolerable by patients.

Figure 1:
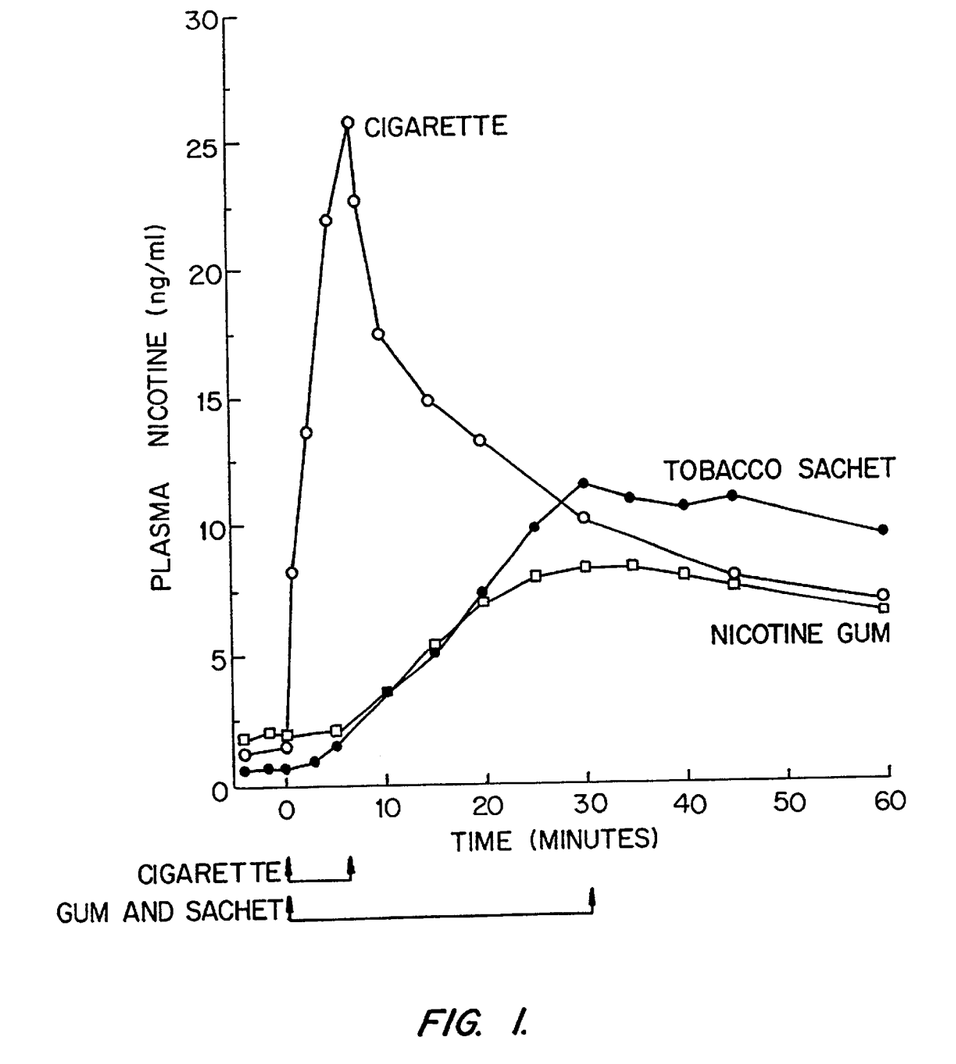
FIG. 1 is a graph of average nicotine plasma levels (nanograms (ng)/milliliter (mL)), resulting from use of cigarettes, tobacco sachets, or nicotine gum, as a function of time (minutes).

Another smokeless version of nicotine delivered to the buccal mucosa is provided by chewing tobacco, oral snuff, or tobacco sachets. Tobacco sachets, which are especially popular in Scandinavia and the U.S., contain ground tobacco in packets that are sucked or held in the mouth. However, as shown in FIG. 1 (cigarette, nicotine gum, and tobacco sachet levels from Russell, M. A. H., Jarvis, M. J., et al. Lancet 1985, 2 1370), use of tobacco sachets results in nicotine blood levels that are more comparable to those resulting from nicotine gum use than from those resulting from cigarette smoking; i.e. they require approximately 30 minutes of use to attain the maximum level of approximately 12 ng/mL, which is less than half of the peak value from smoking one cigarette. One possible reason that nicotine from tobacco sachets is absorbed so slowly is that nicotine is released slowly into the mouth as with nicotine gum; another may be that a significant proportion of the nicotine is swallowed, and therefore subject to the first pass effect of the stomach and liver. In any case, these oral delivery forms may be useful for producing low, steady-state nicotine blood levels, but they do not provide the peak levels needed to satisfy craving.

The literature describes other capsules, tablets, and lozenges for oral delivery of nicotine. For example, WO 8803803 discloses a chewable capsule filled with a liquid containing 0.1–10.0 mg of nicotine, together with additives for improving flavor and dispersion. The capsules are provided in a variety of pH values to allow the patient a choice of nicotine absorption rate, and are especially intended as an aid to quitting smoking.

Another nicotine capsule formulation is disclosed by M. E. Jarvik et al. (in *Clin. Pharm. Ther.* 1970, 11, 574–576) for ingestion as a smoking cessation aid. These capsules, however, were apparently swallowed whole by the subjects, according to the theory that intestinal absorption of nicotine could produce significant blood levels. The study showed a small but significant decrease in the number of cigarettes smoked by subjects, but no quantitative measurements of nicotine blood levels were obtained.

The literature also describes different designs of tablets for delivering nicotine to the mouth and digestive system. BE 899037 discloses a tablet containing 0.1 to 5 mg nicotine as a base or water-soluble acid salt as an aid for quitting smoking.

Wesnes and Warburton (in *Psychopharmacology* 1984, 82, 147–150; and *Psychopharmacology* 1986, 89, 55–59) discuss the use of nicotine tablets in experiments examining the effects of nicotine on learning and information processing. In the first experiment, nicotine was added to dextrose tablets with a drop of tabasco sauce added to disguise the taste of nicotine. In the second experiment, nicotine was added to magnesium hydroxide tablets, under the theory that an alkaline environment in the mouth would enhance buccal absorption. Again, tabasco sauce was added to the tablets to mask the taste of nicotine in both active and placebo tablets. The subjects were instructed to hold the tablets in the mouth for 5 minutes before swallowing, in order to maximize contact with the buccal mucosa.

Shaw (for example in GB 2142822 and U.S. Pat. No. 4,806,356) describes a nicotine lozenge prepared from a mixture of inert filler material, a binder, and either pure nicotine or a nicotine-containing substance by cold compression. The lozenges are intended to be held in the mouth as they dissolve slowly and release nicotine gradually in the buccal cavity.

WO 9109599 describes a nicotine product for oral delivery in the form of an inclusion complex of nicotine and a cyclodextrin compound. The patent also discusses the use of various excipients and direct compression for manufacture of the product.

In recent years, several nicotine lozenges have been commercialized and are available as over-the-counter products in the U.K. Resolution® lozenges, manufactured by Phoenix Pharmaceuticals and distributed by Ernest Jackson, contain 0.5 mg nicotine, together with the anti-oxidant vitamins A, C, and E. Stoppers® lozenges, distributed by Charwell Pharmaceuticals Ltd., contain 0.5 mg nicotine and are available in chocolate, orange and peppermint flavors.

Since nicotine has an acrid, burning taste, these nicotine lozenges typically are formulated with sugar as a major component. However, weight gain after smoking cessation has been identified as a significant factor contributing to smoking relapse. According to a recent survey, current smokers who had tried to quit were asked to judge the importance of several possible reasons for their return to smoking. Twenty-seven percent reported that "actual weight gain" was a "very important" or "somewhat important" reason why they resumed smoking: twenty-two percent said that "the possibility of gaining weight" was an important reason for their relapse. See The Health Benefits of Smoking Cessation: A Report of the Surgeon General, Executive Summary (1990). Thus, sugar-based nicotine lozenge formulations may be unacceptable for a smoking cessation program for those subjects concerned with weight gain.

To date, it has been difficult to deliver nicotine in a profile mimicking the nicotine blood levels achieved by consistent smoking, to satisfy cravings for nicotine in people who are attempting to quit smoking, and thus, to provide greater protection against relapse than other nicotine replacement therapies for people who are trying to quit smoking. It is therefore desirable to provide improved lozenge compositions and methods which avoid the disadvantages of these conventional nicotine delivery devices and methods while providing an effective means for delivering nicotine.

SUMMARY OF THE INVENTION

The present invention provides for the use of nicotine lozenges containing nonnutritive sweeteners as a method of reducing craving for nicotine and of smoking cessation therapy. More specifically, the present invention provides a novel method for producing transient blood levels of nicotine mimicking the effects of cigarette smoking, comprising the periodic use of nicotine lozenges, preferably comprising nicotine, an absorbent excipient, and a nonnutritive sweetener, and more preferably a combination of nonnutritive sweeteners, to provide rapid delivery of nicotine to the buccal mucosa. The nicotine lozenges are designed to be held in the patient's mouth and sucked, and to release nicotine into the buccal cavity. In a preferred embodiment, the nicotine is released rapidly with maximum nicotine blood levels occurring from 2 to 30 minutes after administration of the lozenge.

The lozenges contain fairly low doses, preferably less than 5 mg, and most preferably from 0.5 to 2.0 mg, of nicotine. In particularly preferred embodiments, the nicotine is dispersed in mannitol or β-cyclodextrin and the lozenge is a buffered formulation, preferably at a pH of 6–11, and more preferably at a pH of 7–9. In the most preferred formulation, the lozenge contains the nonnutritive sweetener xylitol, known for its noncariogenic properties, in combination with the sweetener ammonium glycyrrhizinate.

DESCRIPTION OF THE PREFERRED EMBODIMENT

I. Terminology

Unless otherwise stated, the following terms used in the specification and claims have the meanings given below:

"Buccal administration" refers to any system or device for oral administration of a drug to a patient that is held in the mouth and is used to deliver a drug through the buccal mucosa and into the patient's body. This term includes, but is not limited to, lozenges, capsules, and tablets.

"Essential oil" refers to a natural oil with a distinctive scent secreted by the glands of certain aromatic plants having terpenes as the major component. Examples of essential oils include, but are not limited to, citrus oils, flower oils (e.g., rose and jasmine), and oil of cloves.

"Nicotine" refers to nicotine free base, i.e., a compound having the formula:

"Nicotine salt" refers to any mono- or bis- pharmaceutically acid addition acceptable salt or metal salt of nicotine.

"Nicotine lozenge" refers to any lozenge, capsule, tablet, or other device for buccal delivery of nicotine.

"Nonnutritive sweetener" refers to a synthetic or natural substance whose sweetness is higher than or comparable to sucrose and which may have properties such as reduced cariogenicity, health benefits for diabetics, or reduced caloric value compared to sugars.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts, see Bundgaard, H., ed., (1985) *Design of Prodrugs,* Elsevier Science Publishers, Amsterdam.

"Pharmaceutically acceptable metal salt" refers to those salts which retain the biological effectiveness and properties of the free bases and which are not biologically or otherwise undesirable, formed with alkali metal ions such as sodium or potassium; alkaline earth metal ions such as calcium and magnesium; and other metal ions such as zinc.

II. The Lozenge

The present invention provides for lozenges used to deliver nicotine to a patient for reducing his craving for nicotine and for smoking cessation therapy, and methods of using nicotine lozenges for this purpose, including but not limited to the embodiments and methods described below. The nicotine lozenge of the present invention comprises any lozenge, tablet, or capsule formulation that delivers nicotine to the buccal cavity, comprising nicotine dispersed in an absorbent excipient and a nonnutritive sweetener.

A. Nicotine

Nicotine is a heterocyclic compound that exists in both a free base and a salt form. The free base is extremely volatile and is absorbed readily through mucous membranes and intact skin. The major problems reported for products based on nicotine free base originate from the volatility of the nicotine, its acrid, burning taste, the irritant sensation of the mucous membranes, and the decomposition of nicotine in the presence of oxygen. Previously, these problems have been alleviated, in part, through the use of nicotine's salt form, i.e., an acid addition salt or metal salt.

Surprisingly, the lozenges described herein can be produced from either the free base or a pharmaceutically acceptable acid addition salt thereof, or any combination thereof. In the exemplary embodiment, nicotine, i.e., the free base form of nicotine, is used.

Regardless of the formulation used, the lozenge contains fairly low doses of nicotine, preferably between 0.5 and 5 mg, and most preferably from 0.5 to 2.0 mg, to avoid accidental overdosage by swallowing the lozenge intact. High doses are not required because the purpose of the nicotine lozenge is to provide a transient blood level peak of nicotine.

B. The Absorbent Excipient

According to the compositions and methods described herein, the nicotine is dispersed in an absorbent excipient. Absorbent excipients are pharmaceutically acceptable substances that are capable 1) of reducing the volatility of the nicotine, for example, through absorption or by the incorporation of nicotine, such as in an inclusion complex, and 2) of being compressed into a lozenge or tablet. Suitable absorbent excipients include, but are not limited to, mannitol; cyclodextrins, including α, β, and γ-cyclodextrin, as well as derivatives of cyclodextrins, such as trimethyl-β-cyclodextrin, dimethyl-β-cyclodextrin, hydroxyethyl-β-cyclodextrin, and hydroxypropyl-β-cyclodextrin; silica preparations, such as the synthetic silica formulation marketed under the trade name syloid™ by W. R. Grace Limited of North Dale House, North Circular Road, London; cellulosic materials, such as Avicel microcellulose manufactured by FMC Corporation; and other conventional binders and fillers used in the food industry, such as acacia powder, gelatin, gum arabic, and sorbitol.

According to some embodiments, the absorbent excipient will serve more than one role in the lozenge formulation. For example, mannitol can function as both a nonnutritive sweetener and an absorbent excipient. Similarly, the absorbent excipient can serve as a flavorant, buffering agent, lubricant, or other component of the lozenge.

The absorbent excipient is typically present in an amount between about 5 and 25% by weight (wt %), preferably in an amount between about 5 and 20 wt %, and more preferably in an amount between about 5 and 15 wt %.

In a preferred embodiment, the absorbent excipient comprises mannitol or β-cyclodextrin.

C. The Nonnutritive Sweetener

The lozenge will also contain a nonnutritive sweetener. Since nicotine has an acrid, burning taste, the choice of a sweetener for a nicotine lozenge can be critical, for many patients do not find the taste of nicotine palatable in lozenge form. Typically, a nonnutritive sweetener or combination of sweeteners will be utilized in the lozenges described herein.

A nonnutritive sweetener is a synthetic or natural sugar substitute whose sweetness is higher than or comparable to sucrose. Table I lists examples of nonnutritive sweeteners and their relative sweetness values.

TABLE I

| Nonnutritive Sweeteners | | | |
| --- | --- | --- | --- |
| Sweetener | Sweetness[1] | Sweetener | Sweetness[1] |
| Saccharin | 400–500 | Invert sugar | 1.1–1.2 |
| Cyclamate | 30–40 | Palantinose | 0.4–0.5 |
| Aspartame | 100–200 | Xylitol | 1.0 |
| Acesulfame | 200 | Sorbitol | 0.5–0.6 |
| Monellin | 2500 | Mannitol | 0.4–0.6 |
| Neohesperidine | 1000 | Maltitol | 0.7–0.9 |
| Palatinit | 0.4–0.5 | — | — |

[1]Sucrose = 1.0

Thus, the nonnutritive sweetener should have a relative sweetness value between about 0.4 and 2500, as compared with sucrose, more typically between about 0.4 and 500, preferably between about 0.4 and 200, and more preferably, between about 0.4 and 2. See Makinen (1988) *Oral Health* 78: 57–66, which is incorporated herein by reference.

In a preferred embodiment, the nonnutritive sweetener is also noncariogenic. The cariogenicity of a substance is dependent upon its susceptibility to fermentation by *Streptococcus mutans* and other oral microorganisms. Dental researchers have long recognized that fermentable sweeteners such as sucrose, glucose, starch, and corn syrup are

[1] Sucrose =1.0 cariogenic or caries causing. The polyol nonnutritive sweeteners, such as xylitol, sorbitol, fructose, invert sugar, palantinose, mannitol, maltitol, palatinit, and ammonium glycyrrhizinate, however, are generally not fermented to any significant degree and are less cariogenic than sucrose. See Olinger presented at the Interphex-USA Conference/Exhibition, New York; May 8–11, 1990.

More specifically, the ability of xylitol to inhibit the development of new caries has been demonstrated in numerous in vitro and in vivo studies. For example, field trials of oral products containing xylitol have suggested that substitution of sucrose by xylitol in products such as chewing gum may aid in prevention of dental caries (see Söderling, E., and Scheinin, A., *Proc. Finn. Dent. Soc.* 1991, 87(2), 217–229). Studies have also revealed that when xylitol-containing confections are consumed as part of a normal diet, in conjunction with accepted oral hygiene practices, new caries incidence is reduced by about 50% to as high as 80%. See Olinger supra.

Moreover, the literature suggests that nonnutritive sweeteners, and particularly xylitol, may be useful as a sugar substitute for weight control, (see U.S. Pat. No. 3,717,711), which is clearly a major concern for people who are quitting smoking. In addition, xylitol as been shown to prolong gastric emptying and decrease food intake in humans. See Shafer et al. (1987) *Am. J. Clin. Nutr.* 45: 744–47. Likewise, because xylitol is not metabolized as a sugar, it has value for use with people who must restrict their sugar intake, such as diabetics (see Maukinen, K., *Oral Health* 1988, 78(9), page 60).

Xylitol also has a cooling effect when it dissolves in the mouth, due to its negative heat of solution. Xylitol's heat of solution is −36.6 cal/g, compared to −28.9 cal/g for mannitol, −26.6 cal/g for sorbitol, and −4.3 cal/g for sucrose (see Olinger, P. M., presented at the Interphex-USA Conference/Exhibition, New York; May 8–11, 1990). Therefore, xylitol is an excellent choice for a sweetener and excipient in a lozenge that needs to be held in the mouth for an extended period of time, and that needs to be taken frequently every day for maximum therapeutic effect.

Frequently a combination of nonnutritive sweeteners will be used. According to one embodiment, a sweetener with temporal sensory properties similar to that of sucrose (i.e., an appearance time of about 4 seconds and an extinction time of 13 seconds, e.g., some of the polyol sweeteners, saccharin, cyclamate and aspartame) will be combined with a sweetener whose sweetness develops slower or persists longer. For example, ammonium glycyrrhizinate, a nonnutritive sweetener with a slight licorice taste, has a taste onset or appearance time of about 16 seconds for ammonium glycyrrhizinate and a taste persistence or extinction time of 69 seconds. Dubois and Lee (1983) *Chem. Sens.* 7: 237–248. Other examples of nonnutritive sweeteners with temporal sensory properties different than that of sucrose include, but are not limited to, neohesperidine dihydrochalcone (appearance time of 9 seconds and an extinction time of 40 seconds) and stevioside (appearance time of 4 seconds and an extinction time of 22 seconds).

Thus, in a preferred formulation, the lozenge will contain a nonnutritive, noncariogenic sweetener, such as xylitol, sorbitol, fructose, invert sugar, palantinose, mannitol, maltitol, and palatinit, either alone or in combination with other nonnutritive sweeteners. More preferably, xylitol, either alone or in combination with a nonnutritive sweetener having an extinction time longer than that of sucrose, such as ammonium glycyrrhizinate, neohesperidine dihydrochalcone, or stevioside, will be used. In an exemplary embodiment, the nonnutritive sweetener will comprise xylitol and ammonium glycyrrhizinate.

The nonnutritive sweetener is typically present in an amount between about 50 and 90 wt %, preferably in an amount between about 70 and 90 wt %, and more preferably in an amount between about 80 and 90 wt %.

D. Other Ingredients

The lozenge preferably is a buffered formulation in order to aid in buccal absorption of nicotine. A preferred formulation is at a pH of about 6–11, and preferably at a pH of about 7–9. Preferred buffered formulations will include sodium carbonate, sodium bicarbonate, sodium phosphate, calcium carbonate, magnesium hydroxide, potassium hydroxide, magnesium carbonate, aluminum hydroxide, and other substances known to those skilled in the art, as well as combinations of the aforementioned substances. In a most preferred formulation, the lozenge will contain sodium carbonate and bicarbonate as buffering agents.

The buffering agent(s) should be present in an amount sufficient to adjust the pH of the lozenge to between 6 and 11, typically, between about 0.1 and 25% by weight (wt %), preferably in an amount between about 0.1 and 10 wt %, and more preferably in an amount between about 0.1 and 5 wt %.

In addition, the lozenge may contain a flavorant, for example, a candy taste, such as chocolate, orange, vanilla, and the like; essential oils such as peppermint, spearmint and the like; or other flavor, such as aniseed, eucalyptus, 1-menthol, carvone, anethole and the like, to mask the taste of nicotine. See Hall et al. *Food Technol.* 14: 488 (1960); 15: 20 (1961); 19: 151 (1965); 24: 25 (1970); 26: 35 (1972); 27: 64 (1973); 27: 56 (1973); 28: 76 (1974); 29: 70 (1974) 31: 65 (1977); 32: 60 (1978); and 33: 65 (1979), each of which is incorporated herein by reference. It may also contain tobacco flavor in order to reproduce some of the sensation of smoking for the user. A small amount of colloidal silica (less than about 1 wt %) typically is added to tablets containing tobacco flavor to aid in manufacturing.

Magnesium stearate and/or hydrogenated vegetable oil may also be added to the formulation as lubricants. Typically, the lubricant will be present in an amount between about 0.1 and 25 wt %, preferably in an amount between about 0.1 and 10 wt %, and more preferably in an amount between about 0.1 and 5 wt %.

The lozenges described herein may also contain a variety of other additives. For example, pharmacologically active ingredients such as sodium monofluorophosphate, sodium fluoride, dextranase, mutanase, hinokitiol, allantoin, aminocaproic acid, tranexamic acid, azulene, vitamin E derivatives, sodium chloride and the like can be added at need. More specifically, since the effects of xylitol and fluoride on dental hygiene are additive, the former can significantly enhance the efficacy of traditional fluoride treatments. Thus, according to one embodiment, fluoride, and more particularly sodium monofluorophosphate or sodium fluoride will be incorporated into a lozenge formulation having xylitol as a nonnutritive sweetener.

In addition, the lozenge may be colored with conventional, pharmaceutically acceptable food coloring agents. Other additives that may be incorporated within the lozenges described herein include, but are not limited to, preservatives, antimicrobial agents, and antioxidants.

E. The Method of Manufacture

The method of manufacture of these lozenges may be any suitable method known in the art, including but not limited to, the addition of a nicotine compound to premanufactured tablets; cold compression of an inert filler, a binder, and either pure nicotine or a nicotine-containing substance (as described in U.S. Pat. No. 4,806,356, herein incorporated by reference); and encapsulation of nicotine or a nicotine compound. See U.S. Pat. No. 5,135,753, herein incorporated by reference, for examples of methods of manufacture of various nicotine lozenges, sublingual tablets, and gelatin capsules. In a preferred embodiment, the lozenges are formed using direct compression. See Example 4 for a discussion of the manufacturing process in which the nicotine is dispersed in mannitol.

According to another embodiment, an in situ inclusion complex is created with nicotine and β-cyclodextrin using a kneading technique. Specifically, a small amount of a nicotine-water solution is added to cyclodextrin and kneaded or mixed. See Szezetli in *Cyclodextrins and Their Inclusion Complexes,* Akademiai Kiado: Budapest, 1992; p. 109; herein incorporated by reference. This method of forming the nicotine-cyclodextrin inclusion complex is preferred as it minimizes the use of solvents or diluents and thus, eliminates a purification step in the manufacturing process. See also Example 5 for discussion of use of the kneading technique with nicotine and β-cyclodextrin.

A further embodiment of the present invention provides for the production of inclusion complexes of both the nicotine and the flavorant. This embodiment is employed, for example, when an essential oil, or other volatile flavorant, such as carvone or menthol, is used in the lozenge formulation. As in the case of the nicotine inclusion complexes described herein, incorporation of the flavorant into cyclodextrin decreases the volatility of the flavorant and increases formulation stability. In addition, as the flavorant is slowly released from the complex during lozenge administration, the flavorant will "last" longer and thus, offset the acrid taste of the nicotine for longer periods of time.

According to this embodiment, a mixture of the nicotine and the flavorant, and optionally water, is added to the cyclodextrin and kneaded. Alternatively, the nicotine inclusion complex and the flavorant inclusion complex can be prepared separately and then mixed prior to lozenge formulation.

According to another embodiment, a portion of the non-nutritive sweetener, preferably xylitol, is utilized to hard coat the nicotine lozenge. Traditional pan coating techniques can be employed. Typically, weight increases of approximately 35% can be accomplished in less than three hours. See, e.g., Olinger supra.

The lozenges may be packaged in such a manner as to aid in maintaining nicotine stability. Preferred packaging methods include strip lamination in a foil-like material such as Barex®, or packaging in blisters using a Teflon-like material such as Aclar®. See also, Hunt et al. (1991) U.S. Pat. No. 5,077,104.

As noted above, nicotine is a volatile substance. Others have reported a short shelf-life for nicotine lozenges due to evaporation of the nicotine, particularly when the ambient temperature is above 15° C. See Belcher et al. (1989) *Brit. J. Med.* 298: 570. The lozenges described herein, however, are stable for extended periods of time at elevated temperatures, as shown below in Table 2. See Example 6 for a discussion of the assay procedure used to determine stability.

TABLE 2

Nicotine Lozenge Stability Data

| Temperature (° C.) | Time (month) | Appearance | Nicotine mg/loz. | Degradation products | Dissolution test 5 min. | Dissolution test 10 min. |
|---|---|---|---|---|---|---|
| — | Initial | White | 1.001 | <0.1% | 89.7% | 99.8% |
| 35 | 1 | Unchanged | 0.996 | <0.1% | 90.3% | 100.0% |
| 35 | 2 | Unchanged | 0.998 | <0.1% | 88.7% | 100.0% |
| 35 | 3 | Unchanged | 1.000 | <0.1% | 92.2% | 99.6% |
| R.T. | 1 | Unchanged | 1.000 | <0.1% | 93.1% | 99.8% |
| R.T. | 2 | Unchanged | 0.986 | <0.1% | 95.3% | 99.9% |
| R.T. | 3 | Unchanged | 1.000 | <0.1% | 94.5% | 100.1% |

The lozenges described herein will typically have a weight of between about 70 and 1000 mg and will contain fairly low doses of nicotine, preferably less than 5 mg, and most preferably from 0.5 to 2.0 mg.

III. Method of Use

The present invention further provides a method of using nicotine lozenges to provide periodic transient blood level peaks of nicotine as an aid in reducing symptoms of craving of nicotine. Typically, the lozenges described herein will be used ad libitum by the patient to alleviate cravings for nicotine as they arise. Thus, this method provides for a means for the patient to self-titrate his administration needs.

More specifically, nicotine cravings depend, in part, upon daily stress patterns, sleep and eating habits and body weight, previous smoking levels, and the like. Thus, the desire or need for lozenges (comparable to the desire to smoke cigarettes) typically will vary during any given day and from day to day, as well as from patient to patient. The methods described herein allow the patient to consume lozenges in the amounts and at the times when he most feels the craving for nicotine. As nicotine craving is considered by some to be the most consistent and most severe factor in preventing a person from quitting smoking, this ability to self-titrate and thus, stave off the craving for nicotine will increase the efficacy of a smoking cessation program.

A variety of methods can be utilized to assess the craving for nicotine, including but not limited to, the nicotine craving test specified by the *Diagnostic and Statistical Manual of Mental Disorders, Revised Third Edition* (DSM-III-R) (see (1991) *J. Am. Med. Assoc.* 266: 3133); the Shiffman-Jarvik Craving Subscale (see O'Connell and Martin (1987) *J. Consult. Clin. Psychol.* 55: 367–371 and Steur and Wewers (1989) *ONF* 16: 193–198, also describing a parallel visual analog test); West et al. (1984) *Br. J. Addic-* tion 79: 215–219; and Hughes et al. (1984) *Psychopharmacology* 83: 82–87, each of which is expressly incorporated herein by reference.

A preferred nicotine craving scale comprises that specified in DSM-III-R. Supra. According to this scale, a subject is asked to rate the severity of his craving for nicotine on a scale between 0 and 4, wherein 0 is none; 1 is slight; 2 is mild; 3 is moderate; and 4 is severe. Using the compositions and methods described herein, the subject should attain at least a one unit, and preferably at least a two unit, decrease in his craving for nicotine as measured by the protocol set forth in DSM-III-R from 2 to 30 minutes after administration of the nicotine lozenge. More preferably, the maximum reduction in craving for nicotine will occur from about 2 to 10 minutes after administration of the nicotine lozenge.

The Shiffman-Jarvik Craving Scale is a six-item, forced-choice, self-report tool that measures cigarette craving. Each item has seven possible responses which correspond to scores ranging from 1 (no craving) to 7 (high craving). A mean score is obtained to determine the respondent's level of craving. A craving typical score measured 48 hours after the initiation of a smoking cessation program is between about 4 and 5; while a two-week follow-up craving scale will typically be between about 3 and 4. Using the compositions and methods described herein, the subject should attain at least a one unit, and preferably at least a two unit, decrease in his craving for nicotine as measured by the protocol set forth in the Shiffman-Jarvik Craving Scale from 2 to 30 minutes after administration of the nicotine lozenge. More preferably, the maximum reduction in craving for nicotine will occur from about 2 to 10 minutes after administration of the nicotine lozenge.

The "craving questionnaire" craving scale employs a five item questionnaire that asks subjects to rate how much they had been missing their cigarettes, how difficult it had been to be without cigarettes, how much they had been aware of not smoking, how preoccupied they had been with thinking about cigarettes, and how much they had craved their cigarettes. The subject responds to each question with a number between 1 and 3, where 1 is low and 3 is high. The ratings are combined to give a single craving score. According to this craving scale, a combined score of between about 9 and 12 is typical. Using the compositions and methods described herein, the subject should attain at least a three unit, and preferably at least a four unit, decrease in his craving for nicotine as measured by the protocol set forth for use with this craving questionnaire from 2 to 30 minutes after administration of the nicotine lozenge. More preferably, the maximum reduction in craving for nicotine will occur from about 2 to 10 minutes after administration of the nicotine lozenge.

Of course, the lozenges can also be used according to a dosage pattern prescribed by a physician. The dosage pattern will vary with the indication. For example, in addition to use in smoking cessation or reduction therapy, the nicotine lozenges described herein can be used for the treatment of Alzheimer's Disease, ulcerative colitis and related conditions, and diseases associated with reduced central cholinergic function, loss of cholinergic neurons, significant reduction in nicotine receptor binding, neurodegenerative dementia, or cognition and memory impairment. See Masterson (1991) U.S. Pat. No. 5,069,904; Wesnes and Warburton (1984) *Psychopharmacology* 82: 147–150; and Warburton et al. (1986) *Psychopharmacology* 89: 55–59.

The lozenge should be administered without holding any other substance, such as food or beverage, in the mouth. It is particularly important that acidic substances or beverages such as fruits, coffee, tea, or fruit juices are not consumed immediately or concurrently with the nicotine lozenge, in order to insure that a basic environment is maintained within the mouth.

The lozenge is preferably held from 2–10 minutes in the mouth as it dissolves completely and releases nicotine into the mouth, and the dissolved nicotine solution is held in the mouth for as long as possible so that the nicotine is absorbed through the buccal mucosa.

Example 7 describes a protocol for measuring nicotine blood levels in patients using the nicotine lozenge of the present invention. Use of the lozenge will result in a transient nicotine blood level peak from 2 to 30 minutes, and more preferably from 2 to 10 minutes, after the lozenge is placed in the mouth.

Figure 2:
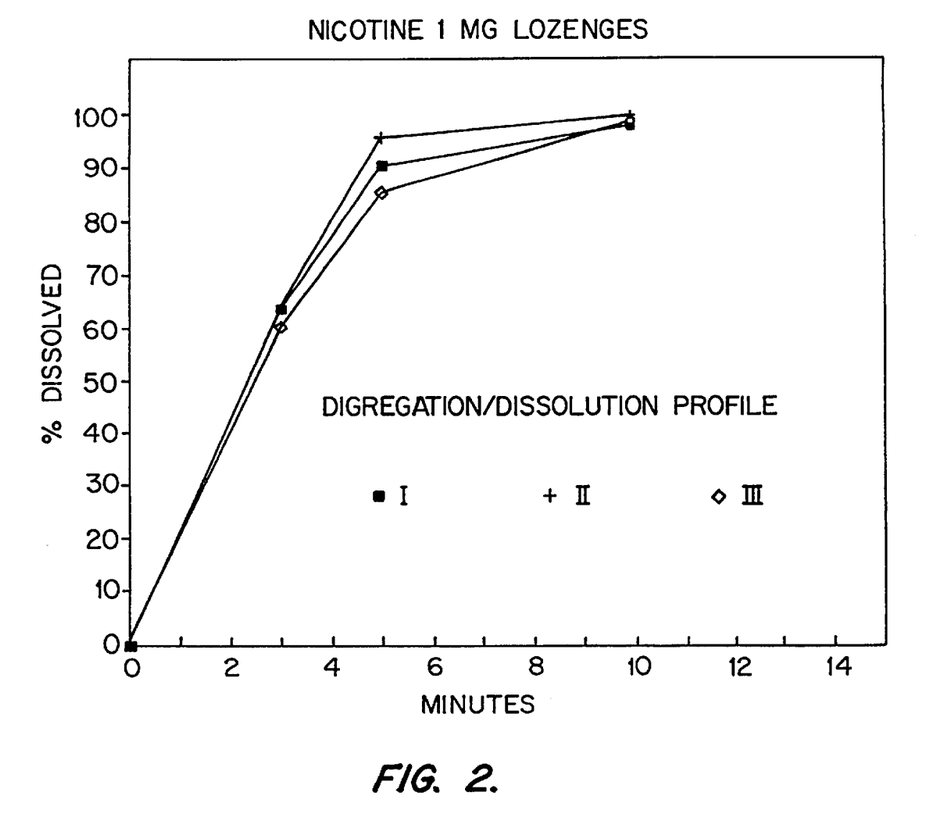
FIG. 2 is a graph of the disintegration/dissolution profiles (weight % dissolved) of three different lozenge formulations, each containing 1 mg nicotine, as a function of time (minutes).

FIG. 2 presents the disintegration/dissolution profiles of the three formulations described in Examples 1–3 (Formulation 1 contains nicotine, mannitol, xylitol, mint flavor, and other excipients; Formulation 2 contains nicotine, mannitol, xylitol, tobacco flavor, and other excipients; and Formulation 3 contains nicotine, cyclodextrin, xylitol, and mint flavor). As shown in FIG. 2, lozenges formulated according to the present invention will be at least 60% dissolved after 3 minutes in the mouth, at least 80% dissolved after 5 minutes, and approximately 100% dissolved after 10 minutes.

Specific examples of the composition of this invention are set forth below.

In order that the invention described herein can be more fully understood, the following examples are set forth. It should be understood that these examples are for illustrative purposes only, and are not to be construed as limiting this invention in any manner.

EXAMPLE 1

Nicotine Lozenge Formulation with Xylitol, Mannitol, and Mint Flavor

| Ingredients | mg/tablet |
| --- | --- |
| Nicotine | 1.0 |
| Mannitol | 200.0 |
| Xylitol | 1309.0 |
| Mint flavor | 20.0 |
| Ammonium glycyrrhizinate | 15.0 |
| Sodium carbonate | 5.0 |
| Sodium bicarbonate | 15.0 |
| Hydrogenated vegetable oil | 25.0 |
| Magnesium stearate | 10.0 |

Manufacturing process
 Nicotine was dispersed in mannitol.
 The powders were mixed.
 The mixture was compressed with a suitable alternative tablet press, using a square 16 mm-punch dosing 1600 mg/tablet.
Packaging
 Tablets were packed into strips of aluminum/Barex.

EXAMPLE 2

Nicotine Lozenge Formulation with Xylitol, Mannitol, and Tobacco Flavor

| Ingredients | mg/tablet |
| --- | --- |
| Nicotine | 1.0 |
| Mannitol | 200.0 |
| Xylitol | 1316.5 |
| Tobacco flavor | 6.0 |

-continued

| Ingredients | mg/tablet |
| --- | --- |
| Colloidal silica | 1.5 |
| Ammonium glycyrrhizinate | 15.0 |
| Sodium carbonate | 5.0 |
| Sodium bicarbonate | 15.0 |
| Hydrogenated vegetable oil | 30.0 |
| Magnesium stearate | 10.0 |

Manufacturing process

Nicotine was dispersed in mannitol.

The powders were mixed.

The mixture was compressed with a suitable alternative tablet press, using a square 16 mm-punch dosing 1600 mg/tablet.

Packaging

Tablets were packed into strips of aluminum/barex.

EXAMPLE 3

Nicotine Lozenge Formulation with Xylitol, β-Cyclodextrin, and Mint Flavor

| Ingredients | mg/tablet |
| --- | --- |
| Nicotine | 1.0 |
| β-cyclodextrin | 109.0 |
| Water | 10.0 |
| Xylitol | 1400.0 |
| Mint flavor | 20.0 |
| Ammonium glycyrrhizinate | 15.0 |
| Sodium carbonate | 5.0 |
| Sodium bicarbonate | 15.0 |
| Hydrogenated vegetable oil | 25.0 |
| Magnesium stearate | 10.0 |

Manufacturing process

Nicotine was dispersed in β-cyclodextrin.

The powders were mixed.

The mixture was compressed with a suitable alternative tablet press, using a square 16 mm-punch dosing 1600 mg/tablet.

Packaging

Tablets were packed into strips of aluminum/barex.

EXAMPLE 4

Manufacturing Process for Nicotine Lozenge Formulation with Xylitol, Mannitol, and Mint Flavor 1) Preparation of the nicotine-mannitol mixture One kg of mannitol was sieved through a 50 mesh sieve and was placed in a Tonazzi mixer. Next, 10 g of nicotine were added slowly with mixing for 10 minutes. The mixture was transferred to a 2 liter amber glass bottle and mixed for 15 minutes in a Turbula mixer.

2) Preparation of the granulate

A quantity of 50.5 g of the mixture from (1) above and 654.5 g of Xilitab 200 (xylitol) were sieved with a 20 mesh sieve, and then were mixed with 50 g mannitol, 5 g magnesium stearate, 12.5 mg Lubritab (hydrogenated vegetable oil), 10 g mint flavor, 7.5 g ammonium glycyrrhizinate, 7.5 g sodium bicarbonate, and 2.5 g sodium carbonate, and was sieved through a 50 mesh sieve. The mixture was transferred to a 2 liter amber glass bottle and mixed for 15 minutes in a Turbula mixer.

3) Tablet formation

The mixture was tabletted in a Belloni alternative press, using a 16-mm$^2$ punch. Tablet weight was 1600 mg/tablet.

4) Packaging

The tablets were packaged into strips of paper/aluminum/Barex.

EXAMPLE 5

Manufacturing Process for Nicotine Lozenge Formulation with Xylitol, β-Cyclodextrin, and Mint Flavor 1) Preparation of the nicotine - β-cyclodextrin complex An initial quantity of 56.76 g of β-cyclodextrin was placed in a 400 mL beaker and 5.68 g of $H_2O$ (equivalent to 10% of the powder) was added with stirring. The water was added in amounts of 1.9 g at a time, with stirring for 10 minutes at each step. The powder, before addition of nicotine, was similar to a wet granulate. Next, 6.37 g of nicotine was added very slowly with stirring, and at the end of the process the granulate was stirred for 10 minutes. The obtained granulate was dried in an oven at 35° C. for 2 hours. A sample was then analyzed for nicotine content.

2) Preparation of the dry granulate

A quantity of 5.25 g of the nicotine - β-cyclodextrin complex, 50 g of β-cyclodextrin, 5 g magnesium stearate, 12.5 g Lubritab® (hydrogenated vegetable oil), 10 g mint flavor, 7.5 g ammonium glycyrrhizinate, 7.5 g sodium bicarbonate, and 2.5 g sodium carbonate were sieved through an 80 mesh sieve. Next, 700 g of Xilitab® 100 (xylitol) was sieved through a 50 mesh sieve. The mixture was mixed in a Turbula mixer for 20 minutes.

3) Tablet formation

The mixture from (2) above was tabletted with a Belloni tablet press equipped with square punches. Tablet weight was 1600 mg/tablet.

4) Packaging

The tablets were put in strips of paper/aluminum/Barex having the following composition: paper 50 g/m$^2$, aluminum 12$\mu$ thickness, 32 g/m$^2$, Barex 35 g/m$^2$.

EXAMPLE 6

Nicotine Lozenge Stability Assay

One nicotine lozenge was crushed and placed in a 50 mL volumetric flask. To the flask was then added tetrahydrofuran (25 mL) and the flask was transferred to a sonicating bath where it was allowed to stand for 20 minutes. Sufficient ethyl acetate was added to bring the solution up to 50 mL. A portion of this solution (1 mL) was removed and placed in a 25 mL volumetric flask. To this flask was then added a few milliliters of water and 0.25 mL of an internal standard solution consisting of 50 mg acetanilide diluted to 100 mL with water. The organic solvents were removed using a gentle nitrogen gas flow which resulted in a cloudy solution. Sufficient water was then added to the cloudy solution to bring the volume of the solution to 25 mL. The solution was then filtered through a 0.22 mcm membrane.

The amount of nicotine in the sample was determined using high performance liquid chromatography (column temperature, 30±1° C.; mobile phase, water:methanol:acetate buffer (0.1 M, pH=4.0):acetonitrile 60:31:7:2, adjusted to pH=6.82 with triethylamine, filtered, and deaerated; mobil phase flow rate, 1.0 mL/min; solid phase, Supelcosil LC1808 (5 mcm) 25 centimeters (cm) ×4.6 millimeters (mm), available from Supelco Inc.; and analytical wavelength 254±1 nanometers (nm)). Under these conditions, nicotine and acetanilide had retention times of about 7.7 and 9.3 minutes, respectively. The ratio of the components in the mobile phase can be varied to provide suitable elution times for the nicotine and the internal standard.

EXAMPLE 7

In Vivo Measurement of Nicotine Release from a Lozenge

A clinical trial of the lozenge described in Example 1 involves six patients who are each given one lozenge on study day 1 at 8:00 a.m. A pre-dose blood sample is taken before each administration. The patients are asked to suck the lozenge. Blood samples are taken at 2.5, 5, 7.5, 10, 15, 20, 25, 30, 45, 60, 75, 90, 105, 120, and 240 minutes. In addition, immediately after the lozenge has dissolved, the patient notifies the medical staff so that the time of dissolution can be recorded.

Blood samples of 5 mL are collected in lithium heparinate tubes. Immediately after collection, the samples are cooled and centrifuged at 4° C. at 1500 rpm for 15 minutes. The plasma is then transferred to polypropylene tubes and stored at −30° C. until analysis for nicotine and cotinine. A capillary gas chromatographic method is used for the analysis of nicotine and cotinine. The detection limit is 0.8 ng/mL for nicotine and 5.0 ng/mL for cotinine. The quantitative determination limit is 1.0 ng/mL for nicotine and 10 ng/mL for cotinine.

The disclosures in this application of all articles and references, including patent documents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A nicotine lozenge consisting of 1 mg nicotine, 200 mg mannitol, 1309 mg xylitol, 20 mg mint flavor, 15 mg ammonium glycyrrhizinate, 5 mg sodium carbonate, 15 mg sodium bicarbonate, 25 mg hydrogenated vegetable oil, and 10 mg magnesium stearate.

2. A nicotine lozenge consisting of 1 mg nicotine, 200 mg mannitol, 1316.5 mg xylitol, 6 mg tobacco flavor, 1.5 mg colloidal silica, 15 mg ammonium glycyrrhizinate, 5 mg sodium carbonate, 15 mg sodium bicarbonate, 30 mg hydrogenated vegetable oil, and 10 mg magnesium stearate.

3. A nicotine lozenge consisting of 1 mg nicotine, 109 mg betacyclodextrin, 10 mg water, 1400 mg xylitol, 20 mg mint flavor, 15 mg ammonium glycyrrhizinate, 5 mg sodium carbonate, 15 mg sodium bicarbonate, 25 mg hydrogenated vegetable oil, and 10 mg magnesium stearate.

* * * * *